United States Patent [19]

Lang et al.

[11] Patent Number: 4,523,821
[45] Date of Patent: Jun. 18, 1985

[54] DEVICE FOR EXAMINING ANTERIOR SECTIONS OF THE EYE

[75] Inventors: Walter Lang; Dieter Müller; Franz Muchel, all of Königsbronn; Roland Wanner, Oberkochen; Peter Niesel, Bollingen, all of Fed. Rep. of Germany

[73] Assignee: Carl-Zeiss-Stiftung, Heidenheim, Fed. Rep. of Germany

[21] Appl. No.: 447,537

[22] Filed: Dec. 7, 1982

[30] Foreign Application Priority Data

Dec. 18, 1981 [DE] Fed. Rep. of Germany ....... 3150124

[51] Int. Cl.³ .......................... A61B 3/10; A61B 3/14
[52] U.S. Cl. .................................. 351/214; 351/205; 351/206
[58] Field of Search ............... 351/205, 206, 207, 208, 351/214; 354/62

[56] References Cited

U.S. PATENT DOCUMENTS 4,171,877 10/1979 Karasawa et al. ................. 351/214

Primary Examiner—Rodney B. Bovernick
Attorney, Agent, or Firm—Hopgood, Calimafde, Kalil, Blaustein & Judlowe

[57] ABSTRACT

In a device for examining anterior sections of the eye, based on the Scheimpflug principle, an electric receiver is provided in the imaging-beam path for electronic evaluation of results of the examination. Various meridian sections in the patient's eye are produced by means of a rotatable prism. A fixation object and a graticule in the illumination beam path enable easy reproducibility of measurement results, as well as facilitating follow-up examinations which seek to observe the same eye for changes, from one examination to a later examination.

5 Claims, 2 Drawing Figures

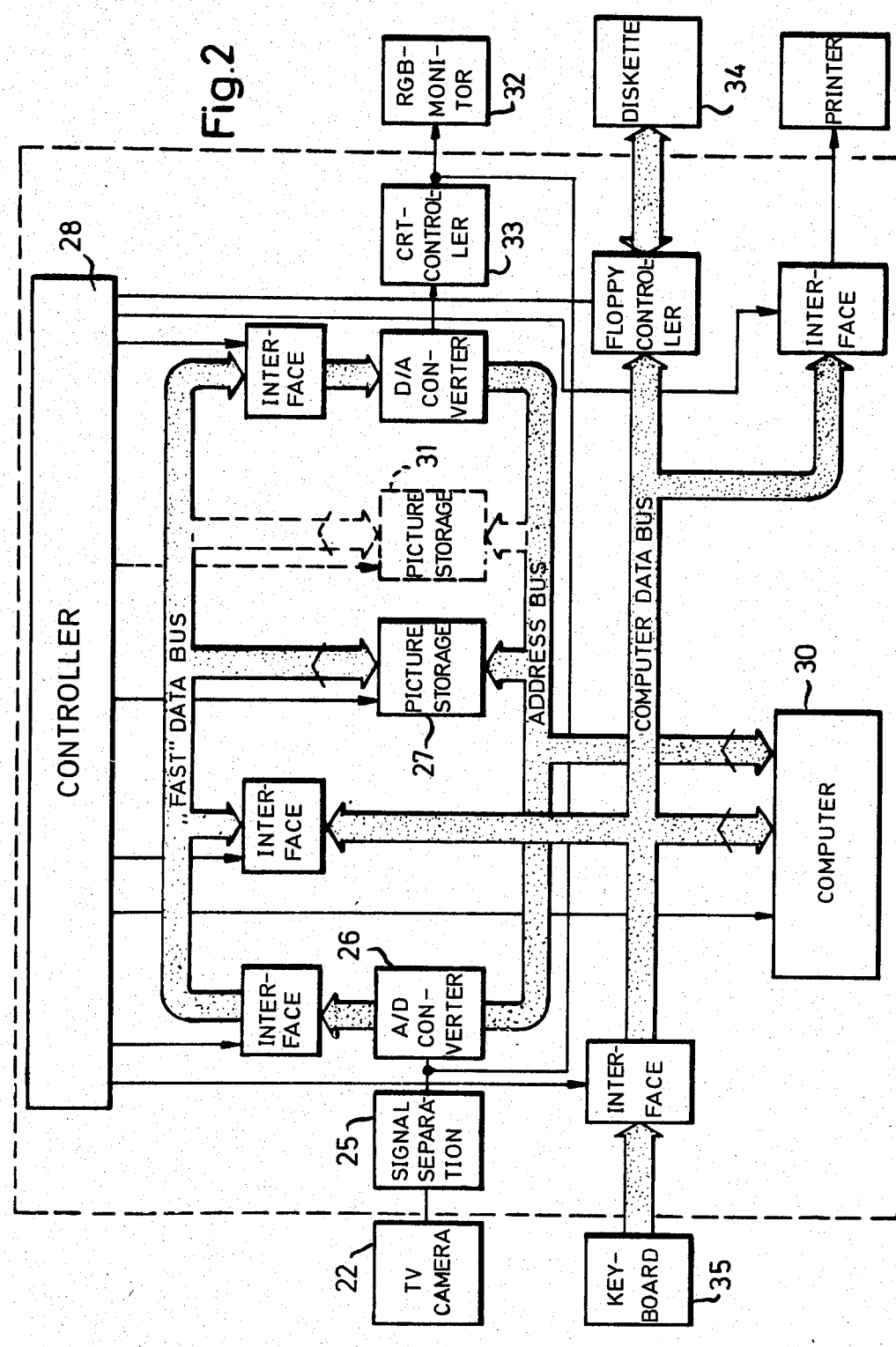

DEVICE FOR EXAMINING ANTERIOR SECTIONS OF THE EYE

BACKGROUND OF THE INVENTION

The present invention relates to a device for examining anterior sections of the eye with a slit-lamp instrument constructed in accordance with the Scheimpflug principle.

In examinations of the human eye by means of a slit-lamp instrument modified in accordance with the Scheimpflug principle, the section plane in a patient's eye is illuminated via slit illumination and is photographed in a photographic direction which is inclined with respect to the plane of the slit lamp. The photographs are evaluated microdensitometrically and give information as to the condition of the lens and cornea of the human eye.

The basic principle of examining the human eye with a slit-lamp instrument developed in accordance with the Scheimpflug principle is known from the journal *Ophthalmologica*, Volume 151, 1965, pages 489–491. But the instrument described in that article was developed for scientific research, and its operation is too complicated for practical use. Furthermore, microdensitometric evaluation of photographs is time-consuming and requires trained personnel.

A slit-lamp instrument in accordance with the Scheimpflug principle and intended for practical use on patients has been described in U.S. Pat. No. 4,171,877. That instrument has the disadvantage that, in order to produce different meridian sections in the eye, the slit lamp and camera must be swung by about 180° in front of the patient's eye. Since observation of the slit image is effected in the semicircle above the horizontal, the upper eyelid of the patient must be kept out of the beam, which is unpleasant for the patient.

BRIEF STATEMENT OF THE INVENTION

The object of the invention is to provide a slit-lamp instrument which is based on the Scheimpflug principle and by which measurements can be carried out in simpler fashion on anterior sections of the eye and of the eye lens. In particular, the instrument is to be capable of detecting the curvature of the anterior surface of the cornea, the thickness of the cornea, the depth of the anterior chamber, and the geometrical dimensions of the lens and its different layers, as well as the gray-scale steps of different zones. Furthermore, the instrument should be uncomplicated to handle and should permit easy reproducibility and evaluation of results of the measurement.

The invention achieves this object by providing, in the illumination beam path of the slit-lamp instrument, a fixation object for the patient's eye and a graticule for localizing the corneal reflex. An electric receiver is provided in the imaging-beam path and, in order to produce different meridian sections in the patient's eye, a prism rotatable about the optical axis and a reversing prism are provided, the slit group being coupled for rotation with the prism and in the same direction.

An aperture diaphragm, an objective and a mirror are preferably rotatably associated with the rotatable prism.

In addition to the electric receiver, means are preferably also provided for mirroring the imaging beam into the observation tube of the illumination beam so that, if desired, the patient's eye can also be directly observed.

The electric receiver in the imaging-beam path may advantageously be a television camera tube connected to a picture data-processing unit. It is also possible to provide picture pick-up sensors as receivers.

The invention is particularly advantageous in that expenditure for precision mechanics and optics is kept small in favor of modern electronic means, and in that mechanically movable parts of the entire instrument are reduced to a minimum. The instrument makes it possible to obtain measurement data of the lens, the cornea and the anterior chamber of the eye, and, by means of data evaluation, to obtain more complex measuring data, such as radii of curvature and surfaces of individual structures.

DETAILED DESCRIPTION

Figure 1:
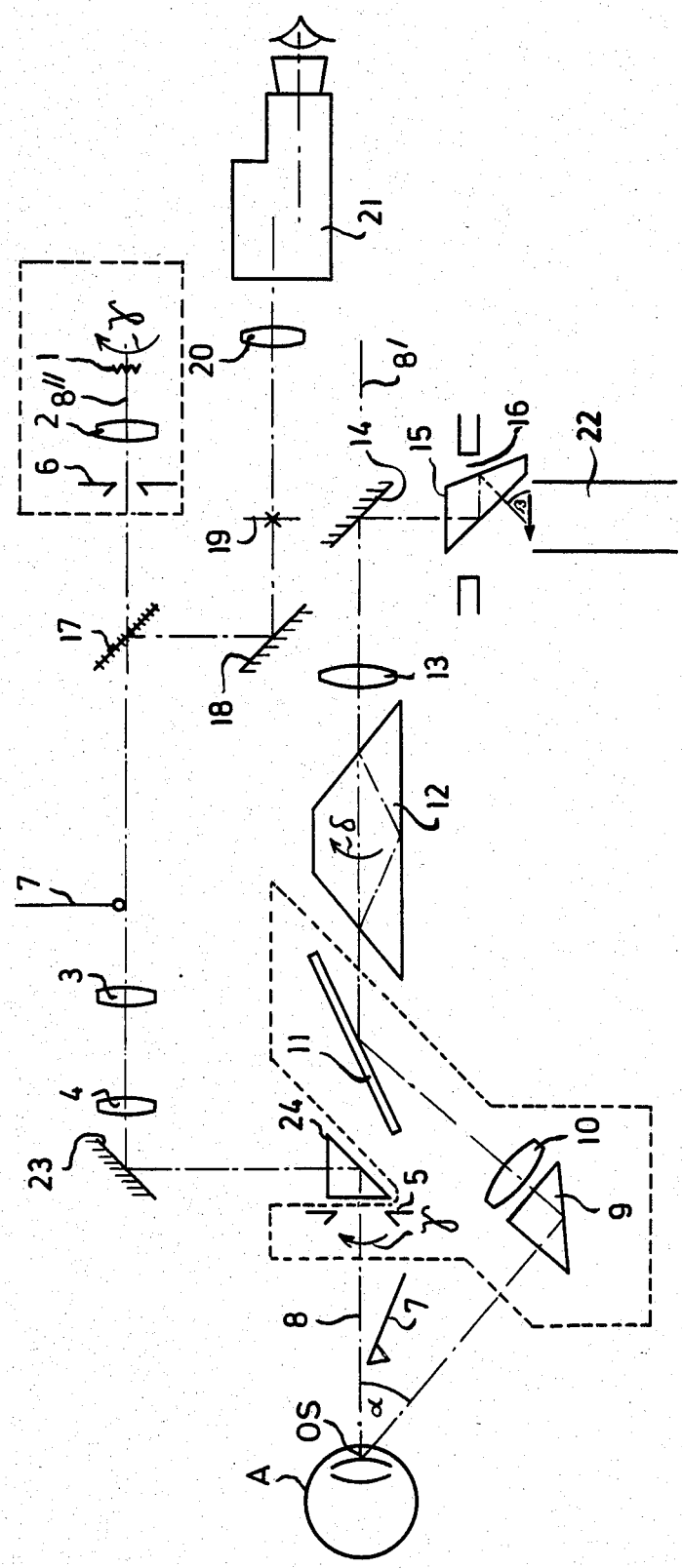

An illustrative embodiment of the invention will be described in conjunction with the accompanying drawings, in which:

FIG. 1 is a diagram, showing optical construction of an instrument of the invention; and FIG. 2 is a block diagram to show picture-data processing, in connection with images produced in the instrument of FIG. 1.

In the optical system of FIG. 1, a lamp filament 1 is imaged, via a Kohler illuminating system (collector 2, condenser lenses 3, 4) and two deflecting elements 23, 24, into an aperture diaphgram 5. The focal length of the condenser lenses is about 125 to 140-mm. A slit 6 produces an optical section OS in the eye A. A fixation object 7 is located at the focal point of condenser lenses 3 and 4 and is focused at infinity, in the direction toward the eye A of the patient under test. The slit image OS is freed of corneal reflex by a bar diaphragm 7' and is imaged, at an angle $\alpha$ to the optical axis 8 of the illumination beam (which is also the axis of symmetry of the eye), via a prism 9, an objective 10, a deflection mirror 11, a reversing prism 12, an objective 13, a deflecting mirror 14 and a prism 15, through the narrow aperture 16 of a television camera, on a receiver tube 22 at an incidence angle $\beta$. The use of prism 15 for deflection of the beam at angle $\beta$ permits arrangement of receiver 22 with its receiving surface perpendicular to the local optical axis, i.e., perpendicular to the axis as reflected by mirror 14, inclined at 45° to the axis of entry to and exit from prism 12. In place of deflection mirrors 11 and 14 deflection prisms can, of course, also be used.

The aperture diaphragm 5 is advisedly not developed as a physical aperture diaphragm at its functional position but is preferably located in the vicinity of the lamp filament and imaged into its functional position. In this way, luminous flux on the fixation object is not impaired by the aperture diaphragm.

In the embodiment shown, the angle $\alpha=40°$ and the angle $\beta=46.5°$. The objective 10 has a focal length $f=88$-mm, and the image scale is 1.2:1. For a different desired image size, the image scale can be changed by selecting a different objective, since the image scale is formed by the quotient of the focal length of objective 13, divided by the focal length of objective 10. By selection of a different image scale, the angle $\beta$ is changed in accordance with the Scheimpflug principle, as is also the position of the mirror 14; eventually, the prism 15 may be dispensed with.

In making a change from one meridian section to another, a first unit, comprising aperture diaphragm 5, prism 9, objective 10 and mirror 11, is bodily rotated about the optical axis 8; the angle of rotation $\gamma$ can be at most 180°. The reversing prism 12 synchronously tracks this rotary displacement at an angle $\delta = \gamma/2$, also about axis 8, as further suggested at 8'. And, a second unit, comprising slit diaphragm 6, collector lens 2 and lamp 1, rotates about its local axis 8'', in 1:1 synchronism with changes in angle $\gamma$. The net result is that the image maintains constant orientation at the image plane of receiver 22, regardless of adjusted change in the angle $\gamma$, i.e., regardless of the orientation of the selected meridian section of the eye.

Corneal reflection from the patient's eye is imaged in the illumination beam via a splitter 17 and a mirror 18 into a graticule 19, where it can be viewed via a lens 20 and a stereoscopic binocular tube 21. In order for stereoscopic observation to be possible in the case of vertical slit imaging, while also keeping imaging depth of the slit image as large as possible in the eye, a width of about 2-mm is selected for the aperture diaphragm. With this width of the aperture diaphgram, only the width of the filament image (8–12 mm) is covered. Over this range, the beam path can be used for stereoscopic viewing. The feature of imaging the corneal reflection at graticule 19 is of great advantage, enabling reproducibility of measurements on patients, as for example, for follow-up examinations. As long as the patient looks at the fixation object 7, the corneal reflection appears at graticule 19, even for repeated measurements. In this way, assurance is had that a given localized area, for example, on the cornea, can be easily found and observed over a long period of time. The fixation object is preferably displaceable in x and y directions normal to the optical axis, and its position with respect to the optical axis is preferably indicated by an illuminated scale.

If visual observation is desired, instead of electronic picture processing, it is readily possible, with the embodiment of FIG. 1, to employ a deflection element in place of mirror 14, to deflect the imaging beam into the observation tube 21.

In the data-evaluation block diagram of FIG. 2, the electric receiver 22 is a television camera having a television camera tube with a sensitive emulsion, for example, a C-Vidicon. The slit-lamp image viewed by the Vidicon is read, via a signal separator and by means of an A/D converter 26, into a picture-storage device 27. A controller 28 provides control signals to coordinate the different bus systems. The capacity of the visual storage is optionally 512×512 bytes or 256×256 bytes. For the display of intensity profiles or density measurements, 8 bits are provided for the gray steps, per picture dot.

A computer 30 is preferably a high-speed 16-bit processor, which permits very rapid program running times. It processes stored image dots with one another and conducts them to a visual-storage device 31, or it displays results at a monitor 32. To provide enhanced contrast, the gray values are processed at 33 as pseudo-colors, and monitor 32 is an RGB monitor. For documentation, for example in therapy follow-ups, a disk storage device 34 is provided. And an input key-board 35 serves for calling up of programs, documentation containing patient data, comments, etc.

As compared with the traditional method, computer-assisted evaluation in use of the invention saves many time-consuming processes, such as, for instance, the developing of film and the measuring of density profiles by means of microdensitometers. And, since the invention provides greater intensity of light and smaller width of the light section, resolving power is also improved.

What is claimed is:

1. A device for examining anterior portions of the eye by a slit-lamp instrument developed on the Scheimpflug principle, in which a fixation object (7) for the eye of a test subject and a graticule (19) for the localizing of the corneal reflex are provided in the illumination beam path, characterized by the fact that in the imaging-beam path an opto-electronic image converter (22) is provided to which an electronic computer for picture data-processing is connected and that, in order to produce different optical meridian sections in the eye of the test subject (a) the opto-electronic image converter (22) is stationary, and (b) in the imaging-beam path a reflecting prism (9) and a reversing prism (12) are each rotatable about the optical axis (8), the respective rotations of the reflecting prism and of the reversing prism being so coupled as to maintain a stationary orientation of the image at the opto-electronic image converter (22) regardless of the instantaneous rotary orientation of the reflecting prism.

2. A device according to claim 1, characterized by the fact that the opto-electronic image converter (22) consists of a television camera tube.

3. A device according to claim 1, characterized by the fact that the illumination-beam path of the slit-lamp instrument includes a lamp (1), a collector (2), a slit diaphragm (6), and an aperture diaphragm (5), the aperture diaphragm being on the optical axis, and that the prism (9) is mounted for bodily rotation with the aperture diaphragm (5) about the optical axis.

4. A device according to claim 3, characterized by the fact that an objective (10) and a mirror (11) are also mounted for bodily rotation with the prism (9) and are positioned to direct the imaging-beam path along the optical axis and to the reversing prism (12).

5. A device according to claim 1, characterized by the fact that the slit-lamp instrument includes an observation tube (21) in the illuminating beam, and by the fact that means are provided for reflecting the imaging beam into the observation tube (21) of the illuminating beam.

* * * * *